US008805003B2

(12) United States Patent
Villain et al.

(10) Patent No.: US 8,805,003 B2
(45) Date of Patent: Aug. 12, 2014

(54) DEVICE AND METHOD FOR LOCALIZING AN OBJECT OF INTEREST IN A SUBJECT

(75) Inventors: Nicolas Francois Villain, Rueil-malmaison (FR); Cecile Anne Marie Picard, Sevres (FR); Nicolas Pierre Bruno Gogin, Paris (FR)

(73) Assignee: Koninklijke Philips N.V., Eindhoven (NL)

( * ) Notice: Subject to any disclaimer, the term of this patent is extended or adjusted under 35 U.S.C. 154(b) by 183 days.

(21) Appl. No.: 12/999,393

(22) PCT Filed: Jun. 18, 2009

(86) PCT No.: PCT/IB2009/052603
§ 371 (c)(1),
(2), (4) Date: Dec. 16, 2010

(87) PCT Pub. No.: WO2009/156918
PCT Pub. Date: Dec. 30, 2009

(65) Prior Publication Data
US 2011/0085706 A1    Apr. 14, 2011

(30) Foreign Application Priority Data
Jun. 25, 2008  (EP) .................................... 08305325

(51) Int. Cl.
*G06K 9/00* (2006.01)
(52) U.S. Cl.
USPC .......................................... 382/103; 382/128
(58) Field of Classification Search
None
See application file for complete search history.

(56) References Cited

U.S. PATENT DOCUMENTS

| 6,317,621 | B1* | 11/2001 | Graumann et al. ............ 600/424 |
| 6,389,104 | B1* | 5/2002 | Bani-Hashemi et al. .. 378/98.12 |
| 6,542,770 | B2* | 4/2003 | Zylka et al. .................... 600/424 |
| 7,050,844 | B2 | 5/2006 | Strobel |
| 2003/0174872 | A1* | 9/2003 | Chalana et al. ............... 382/128 |
| 2003/0187358 | A1* | 10/2003 | Okerlund et al. ............. 600/443 |
| 2003/0220555 | A1* | 11/2003 | Heigl et al. ................... 600/407 |
| 2004/0087850 | A1* | 5/2004 | Okerlund et al. ............. 600/407 |
| 2005/0080328 | A1* | 4/2005 | Vass et al. ..................... 600/407 |
| 2005/0203385 | A1* | 9/2005 | Sundar et al. ................. 600/427 |
| 2006/0023840 | A1 | 2/2006 | Boese |
| 2006/0079759 | A1* | 4/2006 | Vaillant et al. ................ 600/424 |

(Continued)

OTHER PUBLICATIONS

Baert, S.A.M., van de Kraats, E.B., van Walsum, T., Viergever, M.A., and Niessen, W.J., Three-Dimensional Guide-Wire Reconstruction From Biplane Image Sequences for Integrated Display in 3-D Vasculature, Oct. 2003, IEEE Transactions on Medical Imaging, vol. 22, No. 10, pp. 1252-1258.*

(Continued)

*Primary Examiner* — Stephen R Koziol
*Assistant Examiner* — Jonathan S Lee

(57) ABSTRACT

A device for localization of an object of interest in a subject includes a registration unit for registering a 3D-representation of the subject having a plurality of segments corresponding to a plurality of structural regions of the subject, with a 2D-image. The registration unit is configured to define a plurality of areas in the image such that at least one area of the plurality of areas is associated with a respective region of the plurality of regions. A localization unit is configured to localize the object, and extract an indication of the object from the image by processing the image. The processing is limited to an object area of the plurality of areas which is associated with a predetermined object region.

20 Claims, 2 Drawing Sheets

(56) References Cited

U.S. PATENT DOCUMENTS

| | | | |
|---|---|---|---|
| 2006/0184006 A1 | 8/2006 | Chen et al. | |
| 2006/0269113 A1* | 11/2006 | Gundel et al. | 382/131 |
| 2007/0081724 A1* | 4/2007 | Zhang et al. | 382/173 |
| 2007/0100223 A1* | 5/2007 | Liao et al. | 600/407 |
| 2008/0037843 A1 | 2/2008 | Fu et al. | |
| 2008/0118115 A1* | 5/2008 | Williamson | 382/128 |
| 2008/0119725 A1* | 5/2008 | Lloyd | 600/424 |
| 2008/0219536 A1* | 9/2008 | Liao et al. | 382/131 |
| 2008/0240536 A1* | 10/2008 | Soubelet et al. | 382/132 |
| 2009/0310842 A1* | 12/2009 | Groth et al. | 382/131 |
| 2010/0172556 A1* | 7/2010 | Cohen et al. | 382/128 |
| 2010/0226537 A1* | 9/2010 | Villain et al. | 382/103 |
| 2012/0087563 A1* | 4/2012 | Ionasec et al. | 382/131 |

OTHER PUBLICATIONS

Rhode, K.S., Hill, D.L.G., Edwards, P.J., Hipwell, J., Rueckert, D., Sanchez-Ortiz, G., Hegde, S., Rahunathan, V., and Razavi, R., Registration and Tracking to Integrate X-Ray and MR Images in an XMR Facility, Nov. 2003, IEEE Transactions on Medical Imaging, vol. 22, No. 11, pp. 1369-1378.*

Weese, J., Penney, G.P., Desmedt, P., Buzug, T.M., Hill, D.L.K., and Hawkes, D.J., Voxel-Based 2-D/3-D Registration of Fluoroscopy Images and CT Scans for Image-Guided Surgery, Dec. 1997, IEEE Transactions on Information Technology in Biomedicine, vol. 1, No. 4, pp. 284-292.*

Liao, R., Xu, N., and Sun, Y., Location Constraint Based 2D-3D Registration of Fluoroscopic Images and CT Volumes For Image-Guided EP Procedures, 2008, Medical Imaging 2008: Visualization, Image-guided Procedures, and Modeling, pp. 1-8.*

"Mapping Techniques for Atrial Fibrillation Ablation" by Jasbir Sra and Masood Akhtar in Curr Probl Cardiol, Dec. 2007, p. 669 to 767.

"Registration of Three-Dimensional Left Atrial Computer Tomographic Images With Projection Images Obtained Using Fluoroscopy" by Jasbir Sra, David Krum, Angela Malloy, Melissa Vass, Barry Belanger, Elisabeth Soubelet, Regis Vaillant and Masood Akhtar, Published in circulation, 2005:112:3763-3768.

* cited by examiner

DEVICE AND METHOD FOR LOCALIZING AN OBJECT OF INTEREST IN A SUBJECT

FIELD OF THE INVENTION

The present invention relates to a device, method and computer program for localizing an object of interest in a subject.

BACKGROUND OF THE INVENTION

A particular field in which often an object of interest like a catheter needs to be localized in a subject like a human body is electrophysiology (EP). Thus, there is a particular relation between the present invention and cardiac electrophysiology (EP) and more specifically X-Ray-guided ablation and pacemaker placement procedures.

In order to automatically locate EP catheters in 3D (e.g. for electro-anatomical or ablation mapping), it may be necessary to track them in two-dimensional X-Ray images and extrapolate the 3D position from the 2D information. Examples of such an approach include: doing the tracking in two simultaneous images provided by a stereo or bi-plane X-Ray system as in U.S. Pat. No. 7,050,844, so that a 3D position may be deduced from the two view angles.

However, tracking of an EP catheter in 2D X-Ray images is difficult in the general case for several reasons, including the following:

In order to allow real-time imaging without exposing the patient to an excessive amount of radiations, the X-Ray dose in fluoroscopic images is generally low and, thus, the image quality is poor.

Many objects which are visible in a fluoroscopic image might be mistaken for EP catheters (e.g. ECG leads and patches, stitches, injection catheters, etc.).

A number of EP catheters may be used at the same time (e.g. for mapping catheters of various shapes, ablation catheter and reference catheters) but not all of them need to be tracked, while they may interfere in the tracking of those of particular interest.

Thus, as usually during EP procedures, many catheters of various types and shapes are used (e.g. reference, mapping or ablation), additional object are present which may be confused with catheters and the image quality of fluoroscopic images provided is rather poor, classical detection and tracking methods are likely fail in capturing the object(s) of interest correctly.

SUMMARY OF THE INVENTION

It is an object of the present invention to provide a device, a method and a computer program which allow for a localization of an object of interest in a subject which is more robust in terms of sensitivity against image quality, confusable objects and/or interfering objects. Preferably, the present invention provides a means for localization being more accurate without increasing the effort needed for image processing or providing a desired localization accuracy with a reduced need for resources like computation power or computation time.

In a first aspect of the present invention a device for localizing an object of interest in a subject is presented that comprises a registration unit for registering a three-dimensional representation of the subject, which comprises a plurality of structural regions of the subject, with a two-dimensional image, wherein the registration unit is adapted for defining a plurality of areas in the image corresponding to the plurality of segments such that at least one area of the plurality of areas is associated with a respective region of the plurality of regions, and a localization unit for localizing the object, wherein the localization unit is adapted for extracting an indication of the object from the image by processing the image, wherein the processing of the image is limited to an object area of the plurality of areas which is associated with a predetermined object region.

In a further aspect of the present invention a method for localizing an object of interest in a subject is presented, comprising the steps of: registering a three-dimensional representation of the subject, which comprises a plurality of segments corresponding to a plurality of structural regions of the subject, with a two-dimensional image, thereby defining a plurality of areas in the image corresponding to the plurality of segments such that at least one area of the plurality of areas is associated with a respective region of the plurality of regions, and localizing the object by extracting an indication of the object from the image by processing the image, wherein the processing of the image is limited to an object area of the plurality of areas which is associated with a predetermined object region.

In a yet further aspect of the present invention a computer program is presented comprising program code means for causing a computer to carry out the steps of a method according to the invention when said computer program is carried out on a computer.

In the context of EP the present invention makes use of anatomical information from a 3D scan of the patient in order to help in spatially localizing EP catheters in fluoroscopic images and in rejecting most objects and structures of no interest in order to make automatic catheter detection, tracking and labeling more robust.

The invention is based on the insight that, for example, a 3D model of an anatomy of a heart (as an example for a three-dimensional representation of a subject) may be registered on a 2D fluoroscopy image (being a particular example of a two-dimensional image), wherein a segmentation of the heart (provided by the three-dimensional model) projected on the two-dimensional X-Ray image delimits regions of interest for the different anatomical parts. Such an identification of regions of interest may then be used to help the detection and tracking of an object of interest related to the region of interest, e.g. an interventional tool like a catheter, in the sequence of two-dimensional fluoroscopic images, provided that the object of interest is positioned in the known anatomical structure, i.e. in the region of interest.

The extracted indication of the object may be provided by different means. One possibility is that the indication just indicates the position of the object (e.g. of a center point or another predetermined feature of the object). Another possibility is that the indication comprises information on the contours of the object or is constituted by the contours, which may for example be highlighted in the image. Further, the indication may be a segmentation or a sub-image of the image indicating the object. In addition, the indication may also include combinations of some or all of the above possibilities.

Examples of a useful implementation of the present invention may include the following:

In an AF procedure the detection of mapping and ablation catheters can be made easier by rejecting all the objects detected outside the projection of the relevant region, e.g. outside of the left atrium.

Pacemaker leads may be differentiated from other catheters (or automatically labeled) by using the fact they do not originate from the same anatomical structure (i.e. structural region).

Once the 2D-3D registration is completed in a given view, all the changes in the X-Ray system geometry may be applied to the registration matrix. By such an adaptation, the projected regions of interest are kept always consistent with the X-Ray view, i.e. the relation between the segments of the three-dimensional representation and the areas of the two-dimensional showing the corresponding structural regions is maintained correct.

Preferably, in particular in the context of using the present invention for EP purposes, the 3D data is registered with 2D X-Ray images so that the corresponding projection of the volume closely matches the 2D images. This gives the position of the patient in the 3D space of the X-Ray system, and thereby of all the anatomical structures that can be segmented in the 3D volume. For instance, an automatic detection of a reference catheter in the coronary sinus may be limited to the projection of this anatomical region onto the fluoroscopic image, which is a very limited region in frontal view. More extensive computations can be done because the search region is reduced and all the other catheters, even very similar, can be rejected for the simple reason that they are in a different anatomical region.

The present invention is illustrated and explained herein in particular by referring to an implementation in the context of electrophysiology. However, it has to be noted that the present invention is not limited to the field of electrophysiology only. The present invention is also advantageously applicable to other fields like stents placement and minimally invasive surgery (e.g. needle biopsy, radiofrequency ablation), for example. In addition, the present invention may also be used in a non-medical context, e.g. in technical fields relating to robotics.

Although a particularly advantageous aspect of the present invention is related to the medical area and the support for medical practitioners during interventional procedures, the subject in which the object of interest is localized in not limited to being a human or animal body. Accordingly, the structural regions to which the segments of the registration correspond may include but are not necessarily limited to anatomical regions or structures of a body.

Furthermore, the plurality of segments may or may not cover the complete subject or subject part. For example, the three-dimensional representation may include segments for only particular regions of the subject, e.g. only segments corresponding to particular elements of a heart. Nevertheless, even in a case where only a single explicit segment, e.g. of a heart, is provided, this may be considered to be a plurality of segments including a first segment, corresponding to the heart, and a second segment, complementary to the first segment, corresponding to the remainder of the body.

In addition, the segmentation may also be non-exclusive, i.e. different segments may partially correspond to the same structural regions. For example, there may be provided a segment corresponding to the blood circuit and another segment corresponding to the thorax. In addition a segment may comprise one or more further sub-segments, which in turn may overlap or include further segments, e.g. a segment corresponding to the blood circuit including a sub-segment corresponding to the heart or a particular vein (region).

In order to achieve an advantageous effect, the three-dimensional representation does not necessarily have to be a perfect or exact representation of the subject, as even an approximating representation exhibiting a certain amount of error between the segmentation and the structural regions of the subject may be used. The same is true for the registration between the representation and the image. However, the more accurate the representation and the registration are, the more precise the limitation of the image processing may be provided.

According to a preferred aspect of the present invention, the device further comprises an interface which is adapted to allow for a selecting of an object region of the plurality of regions of the subject by a user to be the predetermined object region. Preferably the device allows for a more versatile determination of the region or regions and corresponding object area or areas to which the processing of the image in order to localize the object of interest is limited. By means of the interface a user is able to input and/or to manipulate information based on which one of the object regions of the subject is identified as the predetermined object region. Thus, the user may adapt the device according to the present invention to the particular needs of the current situation the user in.

According to another preferred aspect of the present invention, the device further comprises a three-dimensional scanner for acquiring the three-dimensional representation of the subject. By providing the device according to the present invention with a three-dimensional scanner it is possible to couple the acquiring of data used for a generation of the three-dimensional representation with the localizing aspect of the present invention. Such a coupling eliminates a need for a check on compatibility between the three-dimensional representation and parameters of the present invention which may arise in cases where the three-dimensional representation used by the device according to the present invention is provided by a external source like a medical database of a patient to be examined.

According to yet another preferred aspect of the present invention, the device further comprises a segmentation unit for segmenting the three-dimensional representation into the plurality of segments corresponding to the plurality of structural regions of the subject. According to this preferred aspect the segmentation unit may adapted particularly in view of any special needs of the present invention, i.e. the segmentation unit may be a dedicated unit designed to meet particular specifications optimized for the present invention.

It has to be noted that even in regard of aspects of the present invention according to which a three-dimensional scanner and/or a segmentation unit is provided, these aspects may still include the option that the respective information (i.e. the three-dimensional representation and/or its segmentation) may be inputted to the device according to the present invention from some external source.

According to another preferred aspect of the present invention, the device further comprises an imaging unit for acquiring the two-dimensional image, wherein the imaging unit is preferably a fluoroscope. It was found to be advantageous that the imaging unit is comprised in the device according to the present invention, in particular allowing for a more direct and real-time connection between the 2D image acquiring and the localizing of an object of interest.

According to a preferred aspect of the present invention, the method further comprises the steps of acquiring the three-dimensional representation of the subject, and acquiring the two-dimensional image.

The device and the method of the present invention may also be provided separately from the actual acquiring of data for the representation, generating of the segmentation and the acquiring of the image(s). However, if the scanner, e.g. regarding computed tomography or a magnetic resonance imaging device, the segmentation unit and/or the fluoroscope (for example) is/are combined into the device of the present invention, the units of the device and/or the steps of the method may be adjusted to each other in order to improve performance.

According to a further preferred aspect of the present invention, the localization unit is adapted to process a fluoroscopic image of the subject. A preferred field of use of the present invention is in the area of electrophysiology in which commonly fluoroscopic images are provided.

According to another preferred aspect of the present invention, the acquiring of the two-dimensional image and the localizing of the object are performed in an interventional procedure, and the acquiring of the three-dimensional representation of the subject is performed in a pre-interventional procedure. In order to provide, for example, a tracking of an object of interest during an interventional procedure like radio-frequency ablation for a treatment of atrial fibrillation, the obtaining of the two-dimensional image or projection of the actual situation inside the subject (body) and the localizing of the object are performed preferably in real-time, i.e. virtually instantaneously and continuously. In such a case, the representation including its segmentation is preferably provided prior to the intervention. Thus, there are fewer time constraints and any adjustment to the registration which might be needed to improve its quality may be completed before the treatment or diagnosis procedure as such is started.

According to yet another preferred aspect of the present invention, the object of interest is an interventional tool, in particular a catheter or pacemaker probe. As indicated above, the present invention is particularly useful in the area of medical interventional procedures, in particular including catheters to be localized.

According to a yet further preferred aspect of the present invention, the device further comprises a labeling unit for labeling the object, wherein the labeling unit is adapted for generating a predetermined indication to be associated to the object in case the object is localized in an area of the plurality of areas which is associated with a predetermined label region. According to this aspect, an automatic labeling of, for example, one or more catheters according to their positions might also be deduced from the projection of the anatomical regions. A particularly useful application of the present invention is the possibility to automatically put labels on the devices detected in 2D fluoroscopy, e.g. on the coronary sinus (CS) catheter in an EP procedure. Not only does the region of interest corresponding to the projection of the CS region help to detect the catheter, but it also gives the identification of the detected catheter in this region, which can appear automatically as a label. Thus, for example, an EP catheter that is positioned in a reference site (e.g. coronary sinus, pulmonary veins) can be detected and labeled more easily using the projection of the corresponding volume of interest which is small enough. It is noted that the label region may be different from the object region. An example of such a situation is that a catheter is localized using the object region/segment corresponding to the heart of the patient, whereas for the regions of the heart further (sub-)segments are provided in order to allow for a more details labeling of the catheter according to its position inside the heart.

Further, it is to be understood that any combination of the dependent claims and/or further features of preferred embodiments described herein with the respective independent claim may also constitute an advantageous embodiment of the invention.

BRIEF DESCRIPTION OF THE DRAWINGS

These and other aspects of the invention will be apparent from and elucidated with reference to the embodiment(s) described hereinafter. In the following drawings FIG. 1 schematically shows a device for localizing an object of interest in a subject according to the present invention.

DETAILED DESCRIPTION OF EMBODIMENTS

Figure 1:
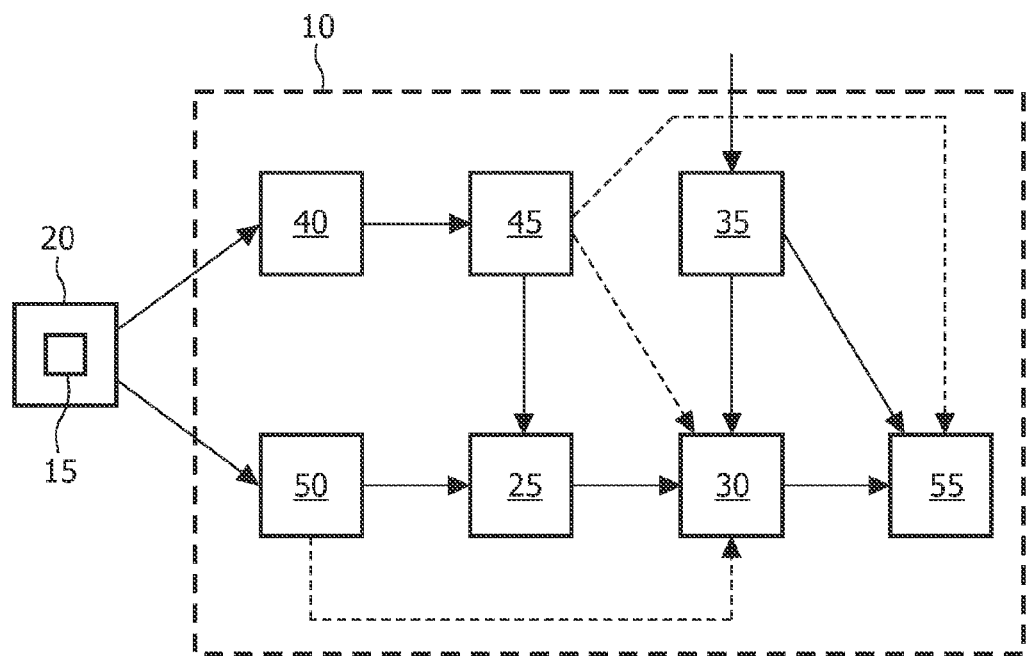

FIG. 1 schematically shows an exemplary device 10 for localizing an object 15 of interest in a subject 20 according to a preferred embodiment of the present invention. The object 15 is provided inside the subject 20, wherein the location of the object 15 inside the subject 20 is to be determined, at least in relation to one or more particular region(s) of the subject 20.

The device 10 includes a magnetic resonance imaging (MRI) device 40 (other embodiments of the present invention may be related to computed tomography (CT) or rotational angiography, for example) acting as a three-dimensional scanner, a segmentation unit 45, coupled to the 3D imaging device 40, a fluoroscope 50 (another example of a 2D imaging device is an ultrasound system) acting as an imaging unit, a registration unit 25, coupled to the segmentation unit 45 and the fluoroscope 50 (according to another embodiment, the registration unit may alternatively or additionally be coupled to a 3D imaging device like the MRI 40), a localization unit 30 coupled to the registration unit 25, an interface 35 coupled to the localization unit 30 and a labeling unit 55, which is coupled to the localization unit 30 and the interface 35. In order to allow for user corrections in other steps, according to a modified embodiment (not shown), the interface is also coupled to the segmentation unit and/or the registration unit.

Several registration methods may be used: The registration may use the segmented model, but it can also be image based (as in a case where the heart is not visible in X-ray images, the result is applied to the segmented areas afterwards) or may even use one or more markers inside or preferably outside the patient body.

The MRI device 40 acquires a three-dimensional scan of the subject 20, preferably before an introduction of the object 15 into the subject 20 and passes the scan to the segmentation unit 45 which processes the scan in order to generate a model or representation of the subject 20 including one or more segments indicating one or more structural regions of the subject 20, to be passed to the registration unit 25.

The fluoroscope 50 provides at least one two-dimensional image of subject 20 indicating an interior constitution of the subject 20, wherein the image includes a sub-image as an indication of the object 15 of interest. The fluoroscope passes the image or a series of images to the registration unit 25.

The registration unit 25 receives the three-dimensional representation (it can be the volume from the 3D imaging device 40 and/or its segmentation from the segmentation unit 45) and the at least one image from the fluoroscope 50 and performs a registration of the representation with the image, wherein a plurality of areas is defined in the image, corresponding to the plurality of segments provided in the representation from the segmentation unit 45, which in turn correspond to respective regions in the subject 20. The data indicating these areas and the 2D image is then passed to the localization unit. In case the registration unit 25 receives a plurality of images, i.e. a series of changing images in temporal order, the registration unit 25 adapts the registration data and/or image area data, preferably for each frame, in order to update the correlation between the images areas of the additional/new image(s) and the representation.

The localization unit 30 receives the data indicating the above areas and the 2D image (or plurality of images). The localization unit 30 may receive the image either from the registration unit 25 (together with the area-data) or directly from the fluoroscope 50 (as indicated by the dashed arrow). Further, the localization unit 30 receives an indication from the interface 35 (inputted by a user (not shown)) regarding the object region, in which the object 15 of interest is to be localized (According to another embodiment, the indication may be omitted, wherein the localization unit is adapted for checking one or more predetermined object regions without the need for a further indication). Based on the provided inputs (i.e. the image, the area data, and the selection of the object region), the localization unit 30 performs an image processing on the image, thereby extracting the sub-image as the indication of the object 15 of interest from the image (According to other embodiments, the indication may for example be a segmentation, a contour and/or a position). This image processing is limited to an object area corresponding to the selected object region.

Due to this limitation of the data to be processed, the image processing may be faster and/or more precise and/or robust without the need for additional computational power.

Further, according to an alternative embodiment (not shown), the interface is coupled to the registration unit and the registration unit passes only a reduced image to the localization unit, in accordance to the limitation of the image processing of the present invention.

According to another alternative embodiment, the registration unit provides a set of parameters as the definition of the areas in the image and passes this set of parameters to the localization unit, whereas the localization unit receives the representation from the segmentation unit (indicated by the dashed line) and provides the limited processing based on the provided set of parameters, the representation and the 2D image. According to this alternative embodiment, the registration unit provides a virtual registration, i.e. the data describing the registration, while the actual registration is provided by the localization unit.

Once the object 15 of interest is localized, the data on the localization is passed to the labeling unit 55, which may be coupled to the segmentation unit 45 in order to receive segmentation data regarding the representation.

Figure 2:
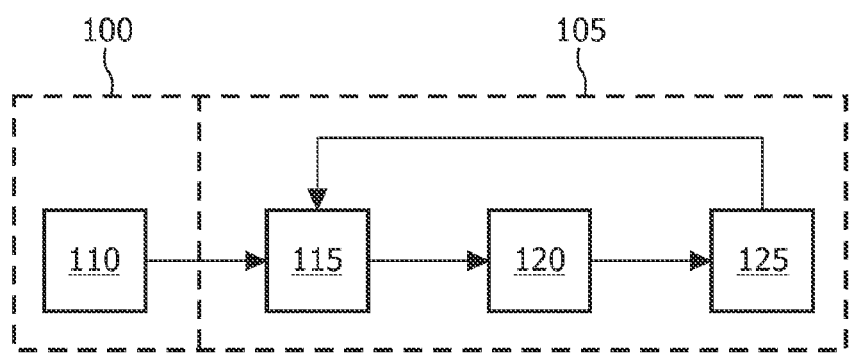
FIG. 2 shows a flow chart schematically illustrating a method for localizing an object of interest in a subject according to the invention.

FIG. 2 shows a flow chart schematically illustrating a method for localizing an object of interest in a subject according to the invention.

The method for localization illustrated in FIG. 2 comprises to general phases, i.e. a pre-interventional phase 100 prior to a treatment and/or diagnosis procedure and an interventional phase 105, in which the localization is performed in real-time during the treatment and/or diagnosis procedure. In step 110, a three-dimensional representation of a subject is obtained and processed (including segmenting). In the subsequent step, step 115, a two-dimensional image of the subject showing the object of interest inside the subject is acquired.

In the following step, step 120, the three-dimensional representation of the subject, which comprises a plurality of segments corresponding to a plurality of structural regions of the subject, is registered with a two-dimensional image, thereby defining a plurality of areas in the image corresponding to the plurality of segments such that at least one area of the plurality of areas is associated with a respective region of the plurality of regions.

Based on the thus obtained registration between the representation and the image, the object of interest is localized in step 125, wherein the localization unit is adapted for extracting a sub-image of the object from the image by processing the image, wherein the processing of the image is limited to an object area of the plurality of areas which is associated with a predetermined object region.

The sequence of steps 115 to 125 may be repeated continuously or at predetermined points in time during the interventional procedure.

Figure 3:
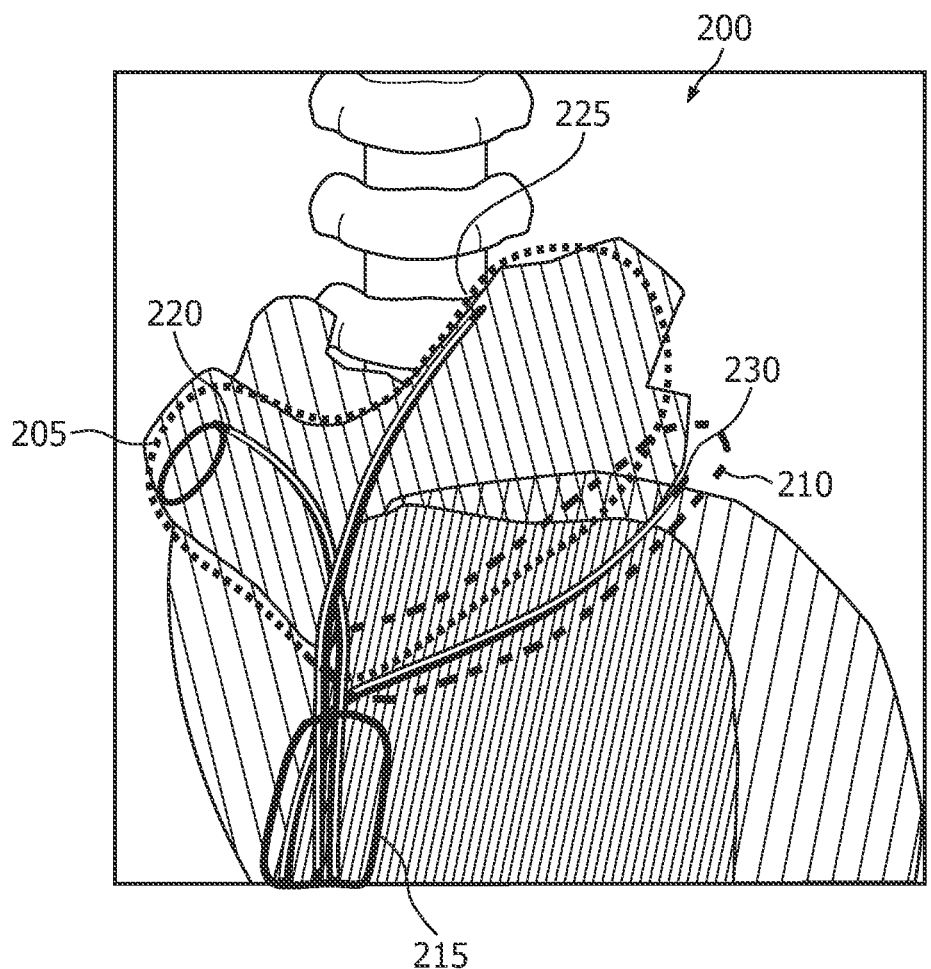
FIG. 3 shows an image of a subject including sub-images of different objects of interest together with indications of respective areas associated with regions of the subject.

FIG. 3 shows an image of a subject including sub-images of different objects of interest together with indications of respective areas associated with regions of the subject. According to an embodiment of the present invention, an image acquisition system is configured to produce 2D fluoroscopy images of an anatomical region, also containing interventional tools such as catheters and/or pacemaker leads. Such a fluoroscopic image 200 is illustrated in FIG. 3. A further image acquisition system is configured to produce a 3D volume of the same anatomical region, in this case the heart. A segmentation of this heart or part of it (atrium, coronary veins . . . ) is made and gives a 3D model. A registration is made between the 3D and 2D datasets and the 3D segmentation can then be projected on the 2D images as illustrated by areas 205, 210 and 215 in FIG. 3. Area 205 corresponds to the left atrium domain, area 210 indicates the coronary sinus domain and area 215 is related to the inferior vena cava domain. Further a plurality of catheters 220, 225 and 230 may also be seen in FIG. 3. The positioning of the model on one frame allows the detection of a reference catheter or lead in a given anatomical site. This site can be the coronary sinus with a long catheter/lead in it or the ostium of one or several pulmonary veins with a "lasso" catheter in it as presented on FIG. 3.

According to the present invention, the computer power and/or computation time needed for an image processing in order to localize a given object like catheters 220, 225, 230 is reduced in comparison to the conventional processing, since the image area to be processed is reduced to the (object area corresponding to the) region of interest the object of interest is provided in. The localization is also easier because other catheters that are not in the considered area may be disregarded during the localization.

Once a catheter/lead is detected on one frame, it can then be tracked on the 2D fluoroscopy sequence.

The person skilled in the art is familiar with the procedures (including algorithms) and the equipment needed or used for implementing the present invention, in particular for acquiring a three-dimensional representation including its segmentation, for acquiring a two-dimensional image of a subject, for registering a three-dimensional representation with a two-dimensional image and for extracting the indication of an object of interest from an image. Therefore a detailed explanation of these aspects is omitted here.

For further background information regarding atrial fibrillation procedures one may refer, for example, to the article "Mapping Techniques for Atrial Fibrillation Ablation" by Jasbir Sra and Masood Akhtar in Curr Probl Cardiol, December 2007, pages 669 to 767. Additional background information on registration may for example be found in "Registration of Three-Dimensional Left Atrial Computed Tomographic Images With Projection Images Obtained Using Fluoroscopy" by Jasbir Sra, David Krum, Angela Malloy, Melissa Vass, Barry Belanger, Elisabeth Soubelet, Regis Vaillant and Masood Akhtar (published in Circulation. 2005; 112:3763-3768).

Electrophysiology (EP) is a specific domain of interventional cardiology where physicians use intra-cardiac catheters to locate and cure electrical dysfunctions of the heart rhythm, usually under X-Ray fluoroscopy guidance. A very challenging EP procedure is radio-frequency ablation for the treatment of atrial fibrillation, also called AF. Another important procedure is the placement of a pacemaker for the cardiac resynchronization therapy (CRT) during which a pacemaker lead has to be placed in a coronary vein. In particular in the context of the conventional devices and methods, electrophysiologists need a special training to perfectly know the anatomy and the access pathways to all the sites of interest and some practice to select the correct devices and manipulate them to target.

The patient's anatomy can be recorded with three dimensional (3D) imaging devices (e.g. CT, MRI) or by injecting contrast agent locally just at the beginning of the intervention (left atrium (LA) and ostium of the pulmonary veins (PV) for AF and coronary veins and sinus for CRT), but the physician has to perform mental registration to navigate in the live fluoroscopy images where this information is not visible anymore.

For AF procedures, knowing the exact positions of the catheters when measuring electrical potentials is key to find the sources that cause fibrillation (ectopic foci, re-entry loop). Even more important is anatomical mapping of the ablation sites in order to perform the desired ablation patterns (such as PV isolation or roof line ablation in LA).

Conventional EP procedures currently guided by fluoroscopy, and particularly AF, often take several hours. The main task of such procedures is to determine the path of electrical potential inside the atrium in order to know where to ablate. Locating precisely the EP catheters in 3D and displaying the recorded electrical potentials or ablation sites superimposed on the 3D atrium anatomy (which is also called electroanatomical mapping or ablation mapping) is of great help for the electrophysiologist.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for localizing an object of interest in a subject comprising:
   a registration unit configured to register a three-dimensional representation of the subject, which comprises a plurality of segments corresponding to a plurality of structural regions of the subject, with a two-dimensional image, wherein the registration unit is configured to define a plurality of areas in the image corresponding to the plurality of segments such that at least one area of the plurality of areas is associated with a respective region of the plurality of structural regions; and
   a localization unit configured to localize the object, wherein the localization unit is configured to extract an indication of the object from the image by processing the image registered with the three-dimensional representation, wherein the plurality of areas are displayed, and wherein an accuracy of localizing the object with reduced computation power or computation time is increased by limiting the processing of the image registered with the three-dimensional representation to an object area of the plurality of areas which is associated with a predetermined object region.

2. The device according to claim 1,
   further comprising an interface which is configured to allow for a selecting of an object region of the plurality of structural regions of the subject by a user to be the predetermined object region.

3. The device according to claim 1,
   further comprising a three-dimensional scanner configured to acquire the three-dimensional representation of the subject.

4. The device according to claim 1,
   further comprising a segmentation unit configured to segment the three-dimensional representation into the plurality of segments corresponding to the plurality of structural regions of the subject.

5. The device according to claim 1,
   further comprising an imaging unit configured to acquire the two-dimensional image, wherein the imaging unit comprises a fluoroscope.

6. The device according to claim 1,
   wherein the localization unit is configured to process a fluoroscopic image of the subject.

7. The device according to claim 1, further comprising
   a labeling unit configured to label the object, wherein the labeling unit is configured to generate a predetermined indication to be associated to the object in case the object is localized in an area of the plurality of areas which is associated with a predetermined label region.

8. A method for localizing an object of interest in a subject comprising the acts of:
   registering a three-dimensional representation of the subject, which comprises a plurality of segments corresponding to a plurality of structural regions of the subject, with a two-dimensional image, thereby defining a plurality of areas in the image corresponding to the plurality of segments such that at least one area of the plurality of areas is associated with a respective region of the plurality of structural regions;
   displaying the plurality of areas in the image; and
   localizing the object by extracting an indication of the object from the image by processing the image registered with the three-dimensional representation; and
   increasing an accuracy of localizing the object with reduced computation power or computation time by limiting the processing of the image registered with the three-dimensional representation to an object area of the plurality of areas which is associated with a predetermined object region.

9. The method according to claim 8, further comprising the acts of:

acquiring the three-dimensional representation of the subject; and acquiring the two-dimensional image.

10. The method according to claim 9, wherein the act of acquiring of the two-dimensional image and the localizing of the object are performed in an interventional procedure, and wherein the act of acquiring of the three-dimensional representation of the subject is performed in a pre-interventional procedure.

11. The method according to claim 8, wherein the object of interest is an interventional tool including one of a catheter and pacemaker probe.

12. A non-transitory computer readable medium embodying computer instructions which, when executed by a processor, configure the processor to perform the acts of:

registering a three-dimensional representation of the subject, which comprises a plurality of segments corresponding to a plurality of structural regions of the subject, with a two-dimensional image, thereby defining a plurality of areas in the image corresponding to the plurality of segments such that at least one area of the plurality of areas is associated with a respective region of the plurality of structural regions;

displaying the plurality of areas in the image; and localizing the object by extracting an indication of the object from the image by processing the image registered with the three-dimensional representation; and increasing an accuracy of localizing the object with reduced computation power or computation time by limiting the processing of the image to an object area of the plurality of areas which is associated with a predetermined object region.

13. The device of claim 1, wherein the indication comprises a segmentation provided by the three-dimensional representation of the subject projected on the two-dimensional image to delimit the object area.

14. The device of claim 1, wherein the indication comprises contours highlighted in the two-dimensional image around the object area.

15. The device of claim 1, wherein the indication comprises a plurality of segmentations projected on the two-dimensional image defining a plurality of areas of interest, and wherein a first segmentation of the plurality of segmentations overlaps a second segmentation of the plurality of segmentations.

16. The method of claim 8, wherein the indication comprises a segmentation provided by the three-dimensional representation of the subject projected on the two-dimensional image to delimit the object area, wherein the segmentation is performed prior to an intervention procedure using the object of interest in the subject, and wherein the projection of the segmentation on the two-dimensional image is performed continuously during the intervention procedure, the method further comprising the acts of deducing a position of the object of interest from the two-dimensional image including the indication; and labeling the position of the object of interest in the two-dimensional image including the indication.

17. The method of claim 8, wherein the indication comprises contours highlighted in the two-dimensional image around the object area.

18. The method of claim 8, wherein the indication comprises a plurality of segmentations projected on the two-dimensional image defining a plurality of areas of interest, and wherein a first segmentation of the plurality of segmentations overlaps a second segmentation of the plurality of segmentations.

19. The non-transitory computer readable medium of claim 12, wherein the indication comprises contours highlighted in the two-dimensional image around the object area.

20. The non-transitory computer readable medium of claim 12, wherein the indication comprises a plurality of segmentations projected on the two-dimensional image defining a plurality of areas of interest, and wherein a first segmentation of the plurality of segmentations overlaps a second segmentation of the plurality of segmentations.

* * * * *